(12) United States Patent
Lobb et al.

(10) Patent No.: US 12,736,537 B2
(45) Date of Patent: Sep. 15, 2026

(54) CANCER DIAGNOSTIC

(71) Applicant: The Council of the Queensland Institute of Medical Research, Herston (AU)

(72) Inventors: Richard Lobb, Herston (AU); Andreas Möller, Herston (AU)

(73) Assignee: The Council of the Queensland Institute of Medical Research, Herston (AU)

( * ) Notice: Subject to any disclaimer, the term of this patent is extended or adjusted under 35 U.S.C. 154(b) by 1106 days.

(21) Appl. No.: 17/771,186

(22) PCT Filed: Oct. 26, 2020

(86) PCT No.: PCT/AU2020/051155
§ 371 (c)(1),
(2) Date: Apr. 22, 2022

(87) PCT Pub. No.: WO2021/077181
PCT Pub. Date: Apr. 29, 2021

(65) Prior Publication Data
US 2022/0365089 A1 Nov. 17, 2022

(30) Foreign Application Priority Data
Oct. 24, 2019 (AU) ................................ 2019904005

(51) Int. Cl.
*G01N 33/575* (2026.01)
*G01N 33/68* (2006.01)

(52) U.S. Cl.
CPC ... *G01N 33/57585* (2026.01); *G01N 33/6848* (2013.01)

(58) Field of Classification Search
None
See application file for complete search history.

(56) References Cited

FOREIGN PATENT DOCUMENTS

| | | | |
|---|---|---|---|
| WO | WO-2018/094469 | A1 | 5/2018 |
| WO | WO-2019/109077 | A1 | 6/2019 |

OTHER PUBLICATIONS

Hoshino et al., "Extracellular Vesicle and Particle Biomarkers Define Multiple Human Cancers," Cell. 182(4):1044-1061, e1-e8, and supplemental content (Aug. 2020) (37 pages).
International Search Report and Written Opinion for International Application No. PCT/AU2020/051155, mailed Dec. 17, 2020 (16 pages).
Leca et al., "Cancer-associated fibroblast-derived annexin A6+ extracellular vesicles support pancreatic cancer aggressiveness," J Clin Invest. 126(11):4140-4156 (Nov. 1, 2016) (18 pages).
Mao et al., "Exosomal nidogen 1 drives liver cancer metastatis by inducing secretion of tumour necrosis factor receptor 1 from activated lung fibroblasts," The International Society for Extracellular Vesicles, 2018 Annual Meeting. Abstract OT03.02, published Apr. 23, 2019 (2 pages).

(Continued)

*Primary Examiner* — Xiaoyun R Xu
(74) *Attorney, Agent, or Firm* — Clark & Elbing LLP

(57) ABSTRACT

The present disclosure relates to the field of cancer. More particularly, the invention relates to methods of diagnosing and treating cancer, including determining a cancer type thereof. These methods involve the detection of markers in an exosome sample of the subject.

22 Claims, 5 Drawing Sheets

(56) References Cited

OTHER PUBLICATIONS

Mitsui et al., "Versican Promotes Tumor Progression, Metastasis and Predicts Poor Prognosis in Renal Carcinoma," Mol Cancer Res. 15(7):884-895 (Jul. 2017).
Perut et al., "Extracellular Nanovesicles Secreted by Human Osteosarcoma Cells Promote Angiogenesis," Cancers. 11(6):779 (Jun. 2019) (17 pages).
Yang et al., "Detection of Tumor Cell-Specific mRNA and Protein in Exosome-Like Microvesicles from Blood and Saliva," PLoS One. 9(11):e110641 (Nov. 2014) (10 pages).
Ying et al., "Knockdown of Pentraxin 3 suppresses tumorigenicity and metastasis of human cervical cancer cells," Scientific Reports. 6(29385):1-12 (Jul. 2016).

CANCER DIAGNOSTIC

RELATED APPLICATIONS

This application claims priority from Australian Patent Application No. 2019904005, filed 24 Oct. 2019, the contents and elements of which are herein incorporated by reference for all purposes.

FIELD OF THE INVENTION

This application relates to cancer. More particularly, this invention relates to methods of diagnosing cancer, including determining a cancer type thereof.

BACKGROUND TO THE INVENTION

Despite screening and therapeutic advancements, the global cancer burden is steadily rising, with 1 in 3 men and 1 in 4 women developing cancer in their lifetime. Furthermore, 1 in 8 men and 1 in 11 women will die from untreatable progression of cancer, making cancer one of the leading causes of death worldwide. There is a significant unmet clinical need to identify patients at an early stage and develop novel therapies to reduce cancer mortality. Early detection of cancers is key as most localised cancers can be cured with surgery alone. Because of this, an improved method of diagnosing cancer in patients from minimally-invasive sampling, such as blood tests, is required. A blood test for cancer should be highly sensitive and specific to be implemented as routine population screening to avoid too many false-positives and -negatives.

SUMMARY OF THE INVENTION

The present invention broadly relates to determining expression levels of one or more exosomal proteins as diagnostic markers of cancer, inclusive of particular cancer types, in a subject. In some aspects, the invention also broadly relates to prognostic methods and the treatment of cancer using such exosomal proteins to inform treatment selection and/or decision making.

In a first aspect, the invention provides a method of diagnosing a cancer or recurrence of a cancer in a subject, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and the expression level of the one or plurality of markers indicates or correlates with a diagnosis or recurrence of the cancer.

In some embodiments, the method of the present aspect further includes the step of determining a cancer type in the subject diagnosed with the cancer.

In some embodiments, a relatively increased expression level of the one or plurality of markers is diagnostic of the cancer or recurrence of the cancer in the subject.

In a second aspect, the invention relates to a method of determining a cancer type in a subject with cancer, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and the expression level of the one or plurality of markers indicates or correlates with the cancer type.

For the method of the first and second aspects, the one or plurality of markers are suitably selected from the group consisting of versican core protein, nidogen-1, pentraxin 3, thrombospondin-1 and any combination thereof. In one particular embodiment, the one or plurality of markers comprise versican core protein, nidogen-1, pentraxin 3 and thrombospondin-1.

In a third aspect, the invention resides in a method of determining the aggressiveness of a cancer in a subject, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and the expression level of the one or plurality of markers indicates or correlates with a level of aggressiveness of the cancer.

In a fourth aspect, the invention provides a method of determining a prognosis for a cancer in a subject, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and an expression level of the one or plurality of markers indicates or correlates with a less or more favourable prognosis for said cancer.

In particular embodiments of the two aforementioned aspects, a relatively decreased expression level of the one or plurality of markers indicates or correlates with a more favourable prognosis and/or a less aggressive cancer; and/or a relatively increased expression level of the one or plurality of markers indicates or correlates with a less favourable prognosis and/or a highly aggressive cancer.

In certain embodiments of the above aspects, the method further includes the step of diagnosing said subject as having: (i) a highly aggressive cancer or a less aggressive cancer; and/or (ii) a less favourable prognosis or a more favourable prognosis.

In a fifth aspect, the invention resides in a method of predicting and/or determining the responsiveness of a cancer to an anti-cancer treatment in a subject, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and an altered or modulated expression level of the one or plurality of markers indicates or correlates with relatively increased or decreased responsiveness of the cancer to the anti-cancer treatment.

The method of the aforementioned aspects suitably includes the further step of treating the cancer in the subject.

In a sixth aspect, the invention relates to a method of treating cancer in a subject, said method including the step of determining an expression level of one or a plurality of markers in an exosomal sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and based on the determination made, initiating, continuing, modifying or discontinuing an anti-cancer treatment.

In certain embodiments, the method of the third, fourth, fifth and sixth aspects includes the further step of determining a cancer type in the subject diagnosed with the cancer.

Referring to the fifth and sixth aspects, the anti-cancer treatment suitably comprises administration to the subject of a therapeutically effective amount of an anti-cancer agent that decreases the expression and/or an activity of the one or plurality of markers.

For the fifth and sixth aspects, the method can include the further step of administering a therapeutically effective amount of the anti-cancer treatment or anti-cancer agent to the subject.

In embodiments of the aforementioned aspects, the method further includes the step of obtaining the exosomal sample from the subject.

In particular embodiments of the above aspects, the method further includes the step of comparing the expression level of the one or plurality of markers in the exosome sample to a reference exosome expression level of the respective one or plurality of markers.

Suitably, the cancer and/or cancer type of the above aspects is selected from the group consisting of lung cancer, such as NSCLC and SCLC, breast cancer, colorectal cancer, prostate cancer, gastric cancer, skin cancer, such as melanoma, brain cancer, such as glioblastoma multiforme (GBM), ovarian cancer, oesophageal cancer and any combination thereof.

In a seventh aspect, the invention relates to a method for identifying or producing an agent for use in the treatment of cancer in a subject including the steps of:

(a) contacting a cell that expresses one or a plurality of markers selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof with a candidate agent; and (b) determining whether the candidate agent modulates the expression and/or an activity of the one or plurality of markers.

In some embodiments, the candidate agent, at least partly, reduces, eliminates, suppresses or inhibits the expression and/or the activity of the marker.

Suitably, for the method of the third, fourth, fifth, sixth and seventh aspects, the one or plurality of markers are selected from the group consisting of versican core protein, nidogen-1, pentraxin 3, thrombospondin-1 and any combination thereof.

In some embodiments of the third, fourth, fifth, sixth and seventh aspects, the method further includes the step of determining an expression level of one or a plurality of further markers, such as thrombospondin-1, in the exosomal sample of the subject.

In an eighth aspect, the invention provides an agent identified or produced by the method of seventh aspect, for use according to the method of the fifth or sixth aspects.

Suitably, the subject of the above aspects is a mammal, preferably a human.

In another aspect, the invention provides a composition comprising an exosomal sample from a subject having or suspected of having cancer, and a reagent for determining the expression level of one or a plurality of VCAN, NID1, PTX3, and THBS1.

In some embodiments, the exosomal sample comprises reagents for determining the level of each of VCAN, NID1, PTX3, and THBS1, in a single composition. In some alternative embodiments, the exosomal sample comprises reagents for determining the level of each of VCAN, NID1, PTX3, and THBS1, in separate compositions.

In yet another aspect, the diagnostic kit or test device comprising 1, 2, 3, 4, 5, 6, 7, 8, 9, 10, or more specific binding members, each of which selectively binds to a marker selected from the group consisting of APOE, PRSS23, VCAN, HAPLN3, COL4A1, NID1, CTGF, COL4A2, CPD, CCBE1, PTX3, SPOCK1, AIMP1, THBS1, and BGN and one or more reagents for detecting said one or more specific binding members or one or more reagents for detecting and/or quantifying formation of a complex formed by said specific binding member and said marker.

In some embodiments, the diagnostic kit or test device is for use in a method of diagnosing cancer or recurrence of cancer in a subject or for determining the type of cancer in the subject.

In some embodiments, the markers comprise VCAN, NID1, PTX3, and THBS1.

In yet another aspect, the present invention provides the use of one or more of: APOE, PRSS23, VCAN, HAPLN3, COL4A1, NID1, CTGF, COL4A2, CPD, CCBE1, PTX3, SPOCK1, AIMP1, THBS1, and BGN, as a marker for determining if a subject is susceptible to treatment with chemotherapeutic agent, optionally wherein the use is as a marker in a method according to any one of the aspects described above or elsewhere herein.

Unless the context requires otherwise, the terms "comprise", "comprises" and "comprising", or similar terms are intended to mean a non-exclusive inclusion, such that a recited list of elements or features does not include those stated or listed elements solely, but may include other elements or features that are not listed or stated.

The indefinite articles 'a' and 'an' are used here to refer to or encompass singular or plural elements or features and should not be taken as meaning or defining "one" or a "single" element or feature. For example, "a" cell includes one cell, one or more cells and a plurality of cells.

DETAILED DESCRIPTION OF THE INVENTION

The present invention is at least partly predicated on the surprising discovery that exosomal proteins identified as upregulated in vitro from normal human bronchial epithelial cells (HBEC) transformed with tumourigenic mutations are accurate diagnostic biomarkers for a broad range of cancers. By way of extension, these exosomal markers may also serve as biomarkers of cancer progression and aggressiveness as well as response to anti-cancer treatment in patients.

Figure 1:
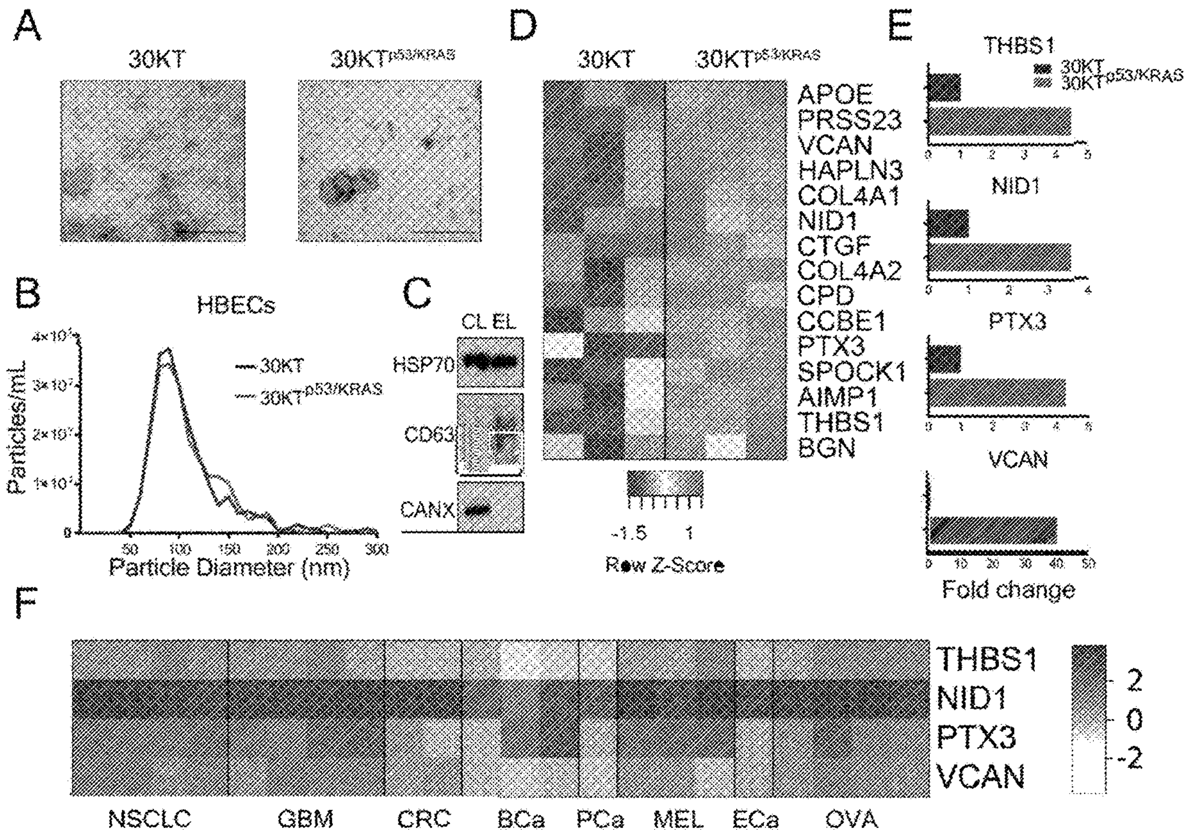
FIG. 1: Oncogenic-induced changes to the protein composition of cell-derived exosomes. (A) The morphology of isolated exosomes was assessed using transmission electron microscopy. Images of normal and transformed HBEC-derived exosomes (Size bar 200 nm). (B) Nanoparticle analysis using tunable resistive pulse sensing (TRPS) of exosomes isolated from HBECs demonstrates the majority of exosomes have a size range between 30 and 150 nm, and that transformation does not result in an increase in exosome secretion. (C) Western blot of exosomes from HBECs demonstrating the presence of exosomes proteins HSP70 and CD63 and the absence of the cell marker calnexin. (D) Quantitative mass spectrometry identified 15 proteins to be significantly upregulated on the extracellular surface of exosomes derived from transformed HBECs (FDR<0.02). (E) Mass spectrometry results were confirmed using ELISA for THBS1, NID1, PTX3 and VCAN normal and transformed HBECs. (F) Exosomes of 22 cell lines from NSCLC, GBM, CRC, BCa, PCa, MEL, ECa, and OVA show a clear increase in expression of THBS1, NID1, PTX3, and VCAN in relation to the expression levels of normal HBEC exosomes.

In a broad form, the present invention relates to a method of diagnosing or detecting cancer, including the recurrence of cancer, in a subject, by determining or measuring an expression level of one or a plurality of markers, such as those provided in FIG. 1, in an exosome sample of the subject.

Accordingly, in an aspect, the invention provides a method of diagnosing a cancer or recurrence of a cancer in a subject, said method including the step of determining an expression level of one or a plurality of markers in an exosome sample of the subject, wherein the markers are selected from the group consisting of apolipoprotein E (APOE; Uniprot Accession No: P02649), serine protease 23 (PRSS23; Uniprot Accession No: 095084), versican core protein (VCAN; Uniprot Accession No: P13611), hyaluronan and proteoglycan link protein 3 (HAPLN3; Uniprot Accession No: Q96S86), collagen type IV alpha 1 chain (COL4A1; Uniprot Accession No: P02462), nidogen-1 (NID1; Uniprot Accession No: P14543), connective tissue growth factor (CTGF; Uniprot Accession No: P29279), collagen type IV alpha 2 chain (COL4A2; Uniprot Accession No: P08572), carboxypeptidase D (CPD; Uniprot Accession No: O75976), collagen and calcium-binding EGF domain-containing protein 1 (CCBE1; Uniprot Accession No: Q6UXH8), pentraxin 3 (PTX3; Uniprot Accession No: P26022), testican-1 (SPOCK1; Uniprot Accession No: Q08629), aminoacyl tRNA synthase complex-interacting multifunctional protein 1 (AIMP1; Uniprot Accession No: Q12904), thrombospondin-1 (THBS1; Uniprot Accession No: P07996), biglycan (BGN; Uniprot Accession No: P21810) and any combination thereof and the expression level of the one or plurality of markers indicates or correlates with a diagnosis or recurrence of the cancer. The proteins defined by these expression numbers are typically those of the human wild-type amino acid sequences, however, reference to the gene or protein may include other mammalian sequences (e.g., mammalian homologues).

In some embodiments, the method of the present aspect further includes the step of determining a cancer type in the subject diagnosed with the cancer.

In a related aspect, the invention relates to a method of determining or diagnosing a cancer type in a subject with cancer, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and the expression level of the one or plurality of markers indicates or correlates with the cancer type.

The terms "diagnosis", "diagnosing" and "diagnostic" refer to methods by which the skilled artisan can estimate and/or determine whether or not a patient is suffering from a given disease or condition, such as a cancer or a particular cancer type. The skilled artisan often makes a diagnosis on the basis of one or more diagnostic indicators, (e.g., an exosomal marker) the presence, absence, amount, or change in amount of which can be indicative of the presence, severity, or absence of the condition. It will also be appreciated that the term "diagnosis" does not refer to the ability to determine the presence or absence of a particular disease, such as cancer, with 100% accuracy, or even that a given course or outcome is more likely to occur than not. Instead, the skilled artisan will understand that the term "diagnosis" refers to an increased probability that a certain disease, disorder or condition, such as cancer or a particular cancer type, is present in the subject.

Accordingly, in particular embodiments, a positive diagnosis of a cancer or a cancer type indicates at least about a 5%, 10%, 15%, 20%, 25%, 30%, 35%, 40%, 45%, 50%, 55%, 60%, 65%, 70%, 75%, 80%, 85%, 90%, 95% or 100% (or any range therein) chance or probability that the cancer or cancer type is present in the subject. The term "about" in this context refers to +/−2%.

As generally used herein, the terms "cancer", "tumour", "malignant" and "malignancy" refer to diseases or conditions, or to cells or tissues associated with the diseases or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumour markers, loss of tumour suppressor expression or activity and/or aberrant or abnormal cell surface marker expression.

Cancers may include any aggressive or potentially aggressive cancers, tumours or other malignancies such as listed in the NCI Cancer Index at http://www.cancer.gov/cancertopics/alphalist, including all major cancer forms such as sarcomas, carcinomas, lymphomas, leukaemias and blastomas, although without limitation thereto. These may include breast cancer, lung cancer inclusive of lung adenocarcinoma and mesothelioma, cancers of the reproductive system inclusive of ovarian cancer, cervical cancer, uterine cancer, testicular cancer and prostate cancer, cancers of the brain and nervous system, head and neck cancers, gastrointestinal cancers inclusive of colon cancer, colorectal cancer, esophageal cancer and gastric cancer, liver cancer, bladder cancer, kidney cancer, skin cancers such as melanoma and skin carcinomas, blood cell cancers inclusive of lymphoid cancers and myelomonocytic cancers, cancers of the endocrine system such as pancreatic cancer, adrenal cancer and pituitary cancers, musculoskeletal cancers inclusive of bone and soft tissue cancers, although without limitation thereto.

In particular embodiments, the cancer and/or cancer type described herein is selected from the group consisting of lung cancer, such as non-small cell carcinoma (NSCLC) (i.e., squamous cell carcinoma, adenocarcinoma and large cell carcinoma), small cell carcinoma (SCLC) and mesothelioma, breast cancer, colorectal cancer, prostate cancer, gastric cancer, skin cancer, such as melanoma, brain cancer, such as glioblastoma multiforme (GBM), ovarian cancer, esophageal cancer and any combination thereof.

As generally used herein, the terms "recurrence" and "cancer recurrence" refer to the return of signs and symptoms of cancer after a period of improvement or remission. In some embodiments, the cancer recurred after a period of time during which the cancer could not be detected, or after the cancer had been at least partly surgically removed, or after growth of the cancer was inhibited by therapeutic treatment. The cancer may reoccur on or come back to the same place as the original (primary) tumour or to another place in the body, such as by way of metastatic recurrence.

As used herein, "metastasis" or "metastatic", refers to the migration or transfer of malignant tumour cells, or neoplasms, via the circulatory or lymphatic systems or via natural body cavities, typically from the primary focus of tumour, cancer or a neoplasia to a distant site in the body, and the subsequent development of one or more secondary tumours or colonies thereof in the one or more new locations. "Metastases" refers to the secondary tumours or colonies formed as a result of a metastasis and encompasses micro-metastases as well as regional, including lymph node, and distant metastases.

In particular embodiments, the method of the present aspect can be utilised to diagnose any minimal residual disease of the cancer. In this regard, the term "minimal residual disease" denotes a small number of cancer cells that remain in a subject during or after treatment when the subject is in remission and typically exhibits no symptoms or signs of the cancer.

As used herein, the term "cancer type" means the type of cancer as determined by the type of tissue in which the cancer originates (histological type) or by primary site, or the location in the body where the cancer first developed or the kind of cell from which it is derived, as well the appearance of the cancer cells.

Interestingly, the Applicants have determined that the expression profile or signature of one or more of the exosomal markers described herein can not only be used to diagnose or detect cancer in a subject, but can also be used to classify or identify the cancer once diagnosed into a specific type and/or subtype of cancer. Accordingly, these exosomal markers may subsequently be used by clinicians to provide an indication of, for example, a cancer aggressiveness, a survival prognosis, a treatment regime, a response to treatment etc that are specific to that particular cancer type diagnosed in the subject.

As used herein, the term "cancer subtype" means a secondary classification of the cancer type, falling within the cancer type. It may be referred to as a molecular classification of cancer. In particular, the cancer subtype may be associated with molecular alterations, cancer survival, distinct clinical and pathological characteristics, specific gene expression signatures, and deregulated signaling pathways.

With respect to determining the cancer type, this may include one or more of the steps of:

(a) calculating or obtaining an expression profile or signature from the one or plurality of exosomal markers described herein in a biological sample, such as an exosome sample from the subject;

(b) comparing the expression profile of the biological sample from the subject to one or more reference expression profiles that correspond to one or more test or reference cancer types; and (c) assigning the expression profile of the biological sample to a cancer type, wherein the cancer type is identified as the test cancer type corresponding to the nearest or most closely aligned reference expression profile of the test cancer type compared with the expression profile of the biological sample from the subject.

In some embodiments, the cancer diagnosis or cancer type is used, at least in part, to determine whether the subject would benefit from treatment of the cancer. By way of example, a patient with a diagnosis of a less aggressive cancer or cancer type may be less likely to suffer from rapid local progression of the cancer and/or metastasis and can be spared from more aggressive monitoring and/or therapy.

In another embodiment, the cancer diagnosis and/or cancer type is used, at least in part, to develop a treatment strategy for the subject. Accordingly, in particular embodiments, the diagnostic methods of the aforementioned aspects are combined with an appropriate treatment plan for the cancer and/or cancer type diagnosed in the subject.

It will be appreciated by the skilled person that exosomes are small (i.e., typically 30-150 nm), cell-derived membrane vesicles of endocytic origin. They may contain lipids, nucleic acid and proteins, and are released into the extracellular environment upon fusion with the plasma membrane. Generally, exosomes are characterized by the presence of marker proteins, including CD63, CD9, HSP70, Flotillin-1 and TSG101, as well as their morphology and size.

In accordance with the methods of the present invention, an exosome sample containing one or more exosomes may comprise or be obtained from most biological fluids including, without limitation, blood, serum, plasma, ascites, cyst fluid, pleural fluid, peritoneal fluid, cerebral spinal fluid, tears, urine, saliva, sputum, nipple aspirates, lymph fluid, fluid of the respiratory, intestinal, and genitourinary tracts, breast milk, intra-organ system fluid, or combinations thereof. To this end, an exosome sample may be isolated or purified from a biological fluid or sample, such as those provided above, so as to facilitate the removal of contaminating proteins, lipoproteins etc.

To this end, an exosome or exosome sample may be isolated by any means known in the art, such as, but not limited to, ultracentrifugation, size-exclusion chromatography, exosome precipitation (e.g., ExoQuick from System Biosciences), affinity-based capture of exosomes (e.g., affinity purification with antibodies to CD63, CD81, CD82, CD9, Alix, annexin, EpCAM, and Rab5) and any combination thereof.

Suitably, the one or plurality of exosomal markers of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1 and/or biglycan may be utilised as a single biomarker or as a combination of any of 2, 3, 4, 5, 6, 7, 8, 9, 10 etc or more (e.g., as an expression profile or signature) of the one or plurality of biomarkers.

In one specific embodiment, the one or plurality of markers are suitably selected from the group consisting of versican core protein, nidogen-1, pentraxin 3, thrombospondin-1 and any combination thereof. Accordingly, in one specific embodiment, the one or plurality of markers comprise versican core protein, nidogen-1, pentraxin 3 and thrombospondin-1.

In particular embodiments, the method of the above aspects includes the further step of determining an expression level of one or a plurality of further markers or biomarkers in a biological sample, such as a blood sample, of the subject.

It is envisaged that the further biomarker may be any as are known in the art that may be utilised in diagnosing or detecting cancer and/or determining a cancer type in a subject. By way of example, the further biomarker may include one or more of the eight circulating protein biomarkers (e.g., cancer antigen 125 (CA-125), carcinoembryonic antigen (CEA), cancer antigen 19-9 (CA19-9), prolactin (PRL), hepatocyte growth factor (HGF), osteopontin (OPN), myeloperoxidase (MPO), and tissue inhibitor of metalloproteinases 1 (TIMP-1)) and/or the tumour-specific mutations in circulating DNA described for the CancerSEEK test (see, e.g., Cohen, Science 2018).

As generally used herein, an expression level of one or more of the exosomal marker proteins identified as upregulated in FIG. 1; may refer to the expression level of a nucleic acid encoding said protein (e.g., RNA, mRNA and cDNA), the protein itself or both, unless otherwise specified.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

By "protein" is meant an amino acid polymer. The amino acids may be natural or non-natural amino acids, D- or L-amino acids as are well understood in the art. As would be appreciated by the skilled person, the term "protein" also includes within its scope phosphorylated forms of a protein (i.e., a phosphoprotein) and/or glycosylated forms of a protein (i.e. a glycoprotein). A "peptide" is a protein having no more than fifty (50) amino acids. A "polypeptide" is a protein having more than fifty (50) amino acids.

Also provided are protein "variants" such as naturally occurring variants (e.g. allelic variants) and orthologs or isoforms of the one or plurality of markers provided herein, such as those listed in FIG. 1. Preferably, protein variants share at least 70% or 75%, preferably at least 80% or 85% or more preferably at least 90%, 91%, 92%, 93%, 94%, 95%, 96%, 97%, 98% or 99% sequence identity with an amino acid sequence of the one or plurality of markers disclosed herein or known in the art. To this end, Accession Numbers referencing an example of a protein sequence of the recited protein marker, as are well understood in the art, are described above and are incorporated by reference herein.

Also provided are protein fragments, inclusive of peptide fragments that comprise less than 100% of an entire amino acid sequence. In particular embodiments, a protein fragment may comprise, for example, at least 10, 15, 20, 25, 30 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1050, 1100, 1150 and 1200 contiguous amino acids of said protein.

As used herein a "gene" is a nucleic acid which is a structural, genetic unit of a genome that may include one or more amino acid-encoding nucleotide sequences and one or more non-coding nucleotide sequences inclusive of promoters and other 5' untranslated sequences, introns, polyadenylation sequences and other 3' untranslated sequences, although without limitation thereto. In most cellular organisms a gene is a nucleic acid that comprises double-stranded DNA.

The term "nucleic acid" as used herein designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylcytosine, methylinosine, methyladenosine and/or thiouridine, although without limitation thereto.

Also included are, "variant" nucleic acids that include nucleic acids that comprise nucleotide sequences of naturally occurring (e.g., allelic) variants and orthologs (e.g., from a different species) of nucleic acids that respectively encode the one or plurality of markers provided herein. Preferably, nucleic acid variants share at least 70% or 75%, preferably at least 80% or 85% or more preferably at least 90%, 91%, 92%, 93%, 94%, 95%, 96%, 97%, 98% or 99% sequence identity with a nucleotide sequence disclosed herein.

Also included are nucleic acid fragments. A "fragment" is a segment, domain, portion or region of a nucleic acid, which respectively constitutes less than 100% of the nucleotide sequence. A non-limiting example is an amplification product or a primer or probe. In particular embodiments, a nucleic acid fragment may comprise, for example, at least 10, 15, 20, 25, 30 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000 and 7500 contiguous nucleotides of said nucleic acid.

As used herein, a "polynucleotide" is a nucleic acid having eighty (80) or more contiguous nucleotides, while an "oligonucleotide" has less than eighty (80) contiguous nucleotides. A "probe" may be a single or double-stranded oligonucleotide or polynucleotide, suitably labeled for the purpose of detecting complementary sequences in Northern or Southern blotting, for example. A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™. A "template" nucleic acid is a nucleic acid subjected to nucleic acid amplification.

As will be understood by the skilled person, the gene and/or protein expression level of the one or more markers provided herein may be relatively (i) higher, increased or greater; or (ii) lower, decreased or reduced when compared to an expression level in a control or reference sample, or to a threshold expression level. In some embodiments, an expression level may be classified as higher increased or greater if it exceeds a mean and/or median expression level of a reference population. In some embodiments an expression level may be classified as lower, decreased or reduced if it is less than the mean and/or median expression level of the reference population. In this regard, a reference population may be a group of subjects who have the same cancer type, subgroup, stage and/or grade as said mammal for which the expression level is determined. In other embodiments, a reference population may be a group of healthy subjects who have been established not to have or be free of cancer. In a further embodiment, a control sample is obtained from the subject in question prior to their being tested for a diagnosis of cancer or cancer type.

Terms such as "higher", "increased" and "greater" as used herein refer to an elevated amount or level of a nucleic acid and/or protein, such as in an exosome sample, when compared to a control or reference level or amount. The expression level of the nucleic acid and/or protein of the one or plurality of markers may be relative or absolute. In some embodiments, the gene and/or protein expression of the one or plurality of markers is higher, increased or greater if its level of expression is more than about 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or at least about 500% above the level of gene and/or protein expression of the respective or corresponding gene and/or protein in a control or reference level or amount.

The terms, "lower", "reduced" and "decreased", as used herein refer to a lower amount or level of a nucleic acid and/or protein, such as in an exosome sample, when compared to a control or reference level or amount. The expression level of the nucleic acid and/or protein of the one or plurality of markers provided herein may be relative or absolute. In some embodiments, the gene and/or protein expression of the one or plurality of markers is lower, reduced or decreased if its level of expression is less than about 95%, 90%, 80%, 70%, 60%, 50%, 40%, 30%, 20% or 10%, or even less than about 5%, 4%, 3%, 2%, 1%, 0.5%, 0.1%, 0.01%, 0.001% or 0.0001% of the level or amount of the gene and/or protein expression of the respective or corresponding gene and/or protein in a control or reference level or amount.

The term "control sample" typically refers to a biological sample, such as an exosome sample, from a (healthy) non-diseased individual not having cancer. In some embodiments, the control sample may be from a subject known to be free of cancer or a sample that was obtained from the subject at an earlier time-point. Alternatively, the control sample may be from a subject in remission from cancer. The control sample may be a pooled, average or an individual sample. An internal control is a marker from the same biological sample (e.g., exosome sample) being tested.

As used herein, a gene and/or protein expression level may be an absolute or relative amount thereof. Accordingly, in some embodiments, the gene and/or protein expression level of the one or plurality of markers provided herein is compared to a control level of expression, such as the level of gene and/or protein expression of one or a plurality of "housekeeping" genes and/or proteins in an exosome sample of the subject.

In further embodiments, the gene and/or protein expression level of the one or plurality of markers is compared to a threshold level of expression, such as a level of gene and/or protein expression in an exosome sample. A threshold level of expression is generally a quantified level of gene and/or protein expression of the one or plurality of markers of the invention. Typically, a gene and/or protein expression level of the one or plurality of markers in an exosome sample that exceeds or falls below the threshold level of expression is predictive of a particular disease state or outcome. The nature and numerical value (if any) of the threshold level of expression will typically vary based on the method chosen to determine the expression of the one or more genes, or products thereof, used in determining, for example, a diagnosis of cancer, a cancer type, a prognosis and/or a response to anti-cancer therapy, in the subject.

A person of skill in the art would be capable of determining a threshold level (e.g., a predetermined threshold) of gene and/or protein expression in an exosome sample that may be used in determining, for example, a diagnosis of cancer, a cancer type, a prognosis and/or a response to anti-cancer therapy, using any method of measuring gene or protein expression known in the art, such as those described herein. In some embodiments, the threshold level is a mean and/or median gene and/or protein expression level (median or absolute) of the one or plurality of markers in a reference population, that, for example, have the same cancer type, subgroup, stage and/or grade as said subject for which the expression level is determined. Additionally, the concept of a threshold level of expression should not be limited to a single value or result. In this regard, a threshold level of expression may encompass multiple threshold expression levels that could signify, for example, a high, medium, or low probability of, for example, metastasis of the subject's cancer.

As used herein, the term "predetermined threshold" refers to a value, above or below which, indicates the responsiveness of a disease to a treatment, or the general prognosis of the disease. For example, for the purposes of the present invention, a predetermined threshold may represent the level or activity of a protein, or the expression level of a protein encoding nucleic acid, in a sample from an appropriate control subject, such as a subject that is known to have a cancer, or susceptible to the recurrence of cancer, or from multiple control subjects or medians or averages of multiple control subjects. Thus, an activity or expression level above or below the threshold indicates the likelihood of the cancer being present in the subject, or the cancer recurring in the subject, or a tumour responding to an anti-cancer therapy, as taught herein. In other examples, a predetermined threshold may represent a value larger or smaller than the level determined for a control subject so as to incorporate further degree of confidence that a level or ratio above or below the predetermined threshold is indicative of the a cancer being present in the subject, or the cancer recurring in the subject, or a tumour responding to an anti-cancer therapy. For example, the predetermined threshold may represent the average or median activity level of the markers disclosed herein in a group of control subjects, plus or minus 1, 2, 3 or more standard deviations. Those skilled in the art can readily determine an appropriate predetermined threshold based on analysis of biological samples from appropriate control subjects.

In some embodiments, a relatively increased expression level of the one or plurality of markers is diagnostic of the cancer or recurrence of the cancer in the subject. In related embodiments, a relatively decreased or relatively unchanged expression level of the one or plurality of markers is diagnostic of the subject not having the cancer or recurrence of the cancer.

The terms "determining", "measuring", "evaluating", "assessing" and "assaying" are used interchangeably herein and may include any form of measurement known in the art, such as those described hereinafter.

Determining, assessing, evaluating, assaying or measuring protein levels of the one or plurality of exosomal proteins may be performed by any technique known in the art that is capable of detecting such proteins whether on the surface or internally expressed in an exosome, or proteins that are isolated, extracted or otherwise obtained from the exosome sample of the subject. These techniques include antibody-based detection that uses one or more antibodies which bind the protein, electrophoresis, isoelectric focusing, protein sequencing, chromatographic techniques and mass spectroscopy and combinations of these, although without limitation thereto. Antibody-based detection may include flow cytometry using fluorescently-labeled antibodies, ELISA, immunoblotting, immunoprecipitation, radioimmunoassay (RIA) and immunocytochemistry, although without limitation thereto.

Determining, assessing, evaluating, assaying or measuring corresponding nucleic acids of the one or plurality of markers provided herein, such as RNA, mRNA and cDNA, may be performed by any technique known in the art. These may be techniques that include nucleic acid sequence amplification, nucleic acid hybridization, nucleotide sequencing, mass spectroscopy and combinations of any these.

Nucleic acid amplification techniques typically include repeated cycles of annealing one or more primers to a "template" nucleotide sequence under appropriate conditions and using a polymerase to synthesize a nucleotide sequence complementary to the target, thereby "amplifying" the target nucleotide sequence. Nucleic acid amplification techniques are well known to the skilled addressee, and include but are not limited to polymerase chain reaction (PCR); strand displacement amplification (SDA); rolling circle replication (RCR); nucleic acid sequence-based amplification (NASBA), Q-β replicase amplification; helicase-dependent amplification (HAD); loop-mediated isothermal amplification (LAMP); nicking enzyme amplification reaction (NEAR) and recombinase polymerase amplification (RPA), although without limitation thereto. As generally used herein, an "amplification product" refers to a nucleic acid product generated by a nucleic acid amplification technique.

PCR includes quantitative and semi-quantitative PCR, real-time PCR, allele-specific PCR, methylation-specific PCR, asymmetric PCR, nested PCR, multiplex PCR, touchdown PCR, digital PCR and other variations and modifications to "basic" PCR amplification.

Nucleic acid amplification techniques may be performed using DNA or RNA extracted, isolated or otherwise obtained from a cell or tissue source. In other embodiments, nucleic acid amplification may be performed directly on appropriately treated cell or tissue samples.

Nucleic acid hybridization typically includes hybridizing a nucleotide sequence, typically in the form of a probe, to a target nucleotide sequence under appropriate conditions, whereby the hybridized probe-target nucleotide sequence is subsequently detected. Non-limiting examples include Northern blotting, slot-blotting, in situ hybridization and fluorescence resonance energy transfer (FRET) detection, although without limitation thereto. Nucleic acid hybridization may be performed using DNA or RNA extracted, isolated, amplified or otherwise obtained from a cell or tissue source or directly on appropriately treated cell or tissue samples.

It will also be appreciated that a combination of nucleic acid amplification and nucleic acid hybridization may be utilized.

It will be appreciated that determining the expression of the one or plurality of markers provided herein may include determining both the nucleic acid levels thereof, such as by nucleic acid amplification and/or nucleic acid hybridization, and the protein levels thereof. Accordingly, detection and/or measurement of expression of the one or plurality of markers from the exosome sample of the subject may be performed by any of those methods or combinations thereof described herein (e.g measuring mRNA levels or an amplified cDNA copy thereof and/or by measuring a protein product thereof), albeit without limitation thereto.

In light of the foregoing, it will further be appreciated that an expression level of the one or plurality of markers provided herein may be an absolute or relative amount of an expressed gene or gene product thereof, inclusive of nucleic acids such as RNA, mRNA and cDNA, and/or protein.

In a further aspect, the invention resides in a method of determining the aggressiveness of a cancer in a subject, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and the expression level of the one or plurality of markers indicates or correlates with a level of aggressiveness of the cancer.

In another aspect, the invention provides a method of determining a prognosis for a cancer in a subject, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and an expression level of the one or plurality of markers indicates or correlates with a less or more favourable prognosis for said cancer.

In certain embodiments of the above aspects, the method further includes the step of diagnosing said subject as having: (i) a highly aggressive cancer or a less aggressive cancer; and/or (ii) a less favourable prognosis or a more favourable prognosis.

By "aggressiveness" and "aggressive" is meant a property or propensity for a cancer to have a relatively poor prognosis due to one or more of a combination of features or factors including: at least partial resistance to therapies available for cancer treatment; invasiveness; metastatic potential; recurrence after treatment; and a low probability of patient survival, although without limitation thereto.

In particular embodiments, the proteins provided herein, such as those provided in FIG. 1, are prognostic for aggressive disease, and in particular a shorter time to pathological recurrence and/or a shorter patient survival time. In further embodiments, the proteins provided herein, such as those provided in FIG. 1, correlate with or indicate metastatic cancer.

The terms "prognosis" and "prognostic" are used herein to include making a prognosis, which can provide for predicting a clinical outcome (with or without medical treatment), selecting an appropriate course of treatment (or whether treatment would be effective) and/or monitoring a current treatment and potentially changing the treatment. This may be at least partly based on determining the gene and/or protein expression levels of the one or plurality of markers by the methods of the invention, which may be in combination with determining the expression levels of additional protein and/or other nucleic acid biomarkers, such as thrombospondin-1 or those hereinbefore described for CancerSEEK. A prognosis may also include a prediction, forecast or anticipation of any lasting or permanent physical or psychological effects of cancer suffered by the subject after the cancer has been successfully treated or otherwise resolved. Furthermore, prognosis may include one or more of determining metastatic potential or occurrence, therapeutic responsiveness, implementing appropriate treatment regimes, determining the probability, likelihood or potential for cancer recurrence after therapy and prediction of development of resistance to established therapies (e.g., chemotherapy). It would be appreciated that a positive prognosis typically refers to a beneficial clinical outcome or outlook, such as long-term survival without recurrence of the subject's cancer, whereas a negative prognosis typically refers to a negative clinical outcome or outlook, such as cancer recurrence or progression.

In some embodiments of the method of the two aforementioned aspects, a relatively decreased or relatively unchanged expression level of the one or plurality of markers indicates or correlates with a more favourable prognosis and/or a less aggressive cancer; and/or a relatively increased expression level of the one or plurality of markers indicates or correlates with a less favourable prognosis and/or a highly aggressive cancer.

In one particular embodiment, the cancer prognosis or aggressiveness is used, at least in part, to determine a likelihood of metastasis of the cancer in said subject.

Suitably, a relatively decreased or unchanged expression level of the one or plurality of markers indicates or correlates with a decreased likelihood of metastasis of said cancer; and/or a relatively increased expression level of the one or plurality of markers indicates or correlates with an increased likelihood of metastasis of said cancer.

In some embodiments, the cancer prognosis or aggressiveness is used, at least in part, to determine whether the subject would benefit from treatment of the cancer. By way of example, a patient with a favourable prognosis and/or a less aggressive cancer may be less likely to suffer from rapid local progression of the cancer and/or metastasis and can be spared from more aggressive monitoring and/or therapy.

In another embodiment, the cancer prognosis or aggressiveness is used, at least in part, to develop a treatment strategy for the subject.

In some embodiments, the cancer prognosis or aggressiveness is used, at least in part, to determine minimal residual disease, disease progression or recurrence in the subject.

In some embodiments, the cancer prognosis or aggressiveness is used, at least in part, to determine an estimated time of survival.

Suitably, the method of the aforementioned aspects further includes the step of diagnosing said subject as having: (i) a highly aggressive cancer or a less aggressive cancer; and/or (ii) a less favourable prognosis or a more favourable prognosis.

In some embodiments, a relatively lower gene and/or protein expression level of the one or plurality of markers provided herein indicates or correlates with relatively increased responsiveness of the cancer to the anti-cancer treatment. In alternative embodiments, a relatively lower gene and/or protein expression level of the one or plurality of markers provided herein indicates or correlates with relatively decreased responsiveness of the cancer to the anti-cancer treatment.

Suitably, the cancer is of a type hereinbefore described, albeit without limitation thereto.

In a further aspect, the invention resides in a method of predicting and/or determining the responsiveness of a cancer to an anti-cancer treatment in a subject, said method including the step of determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof and an altered or modulated expression level of the one or plurality of markers indicates or correlates with relatively increased or decreased responsiveness of the cancer to the anti-cancer treatment.

As would be understood by the skilled person, the expression level of a gene or protein may be deemed to be "altered" or "modulated" when the expression level is higher/increased or lower/decreased when compared to a control or reference sample or expression level, such as a threshold level. In some embodiments, the expression level may be classified as high if it is greater than a mean and/or median relative expression level of a reference population and the expression level may be classified as low if it is less than the mean and/or median expression level of the reference population. In this regard, a reference population may be a group of subjects who have the same cancer type, subgroup, stage and/or grade as said mammal for which the expression level is determined. Furthermore, the expression level may be relative or absolute.

In some embodiments, the one or plurality of markers are selected from the group consisting of versican core protein, nidogen-1, pentraxin 3, thrombospondin-1, and any combination thereof. More particularly, the one or plurality of markers suitably comprise versican core protein, nidogen-1 and pentraxin 3 and optionally further include the further biomarker of thrombospondin-1.

In some embodiments, a relatively higher expression level of the one or plurality of markers indicates or correlates with relatively increased responsiveness of the cancer to the anti-cancer treatment. In alternative embodiments, a relatively higher expression level of the one or plurality of markers indicates or correlates with relatively decreased responsiveness of the cancer to the anti-cancer treatment.

In some embodiments, the expression level of the one or plurality of markers, such as a relatively higher expression level thereof, indicates or correlates with the continued presence (e.g., minimal residual disease), progression or recurrence of the cancer or a lack of or reduced responsiveness of the cancer to the anti-cancer treatment.

In some embodiments, the methods of the invention include assessing the activity, expression, or amount of one or more biomarker in subject, or in a sample (e.g., an exosome sample) derived from the subject, to obtain a sample profile of the more or more biomarker; and making a prediction based on the sample profile of the one or more biomarker. Optionally, the prediction is made by comparing the sample profile to a control profile. For example, a suitable control profile that may be used is: (i) obtained from a population of control subjects having cancer; or (ii) obtained from a control subject or population of control subjects having cancer that is a recurred cancer; (iii) a predetermined profile of "average, median, or mean" or "standard ranges" of biomarker expression, activity, or amount values obtained from a control subject or population of control subjects having cancer; (iv) obtained from a control sample having a known "average, median, or mean" value of biomarkers indicative of a control subject or population of control subjects having cancer; (v) a predetermined profile of biomarker expression, activity or amount "threshold" values obtained from a control subject or population of control subjects having cancer; or (vi) obtained from a control sample having a known "threshold" value of biomarkers indicative of a control subject or population of control subjects having cancer.

With respect to the invention of the aforementioned aspects, the method suitably includes the further step of treating the cancer in the subject.

Further aspects of the invention relate to treatment of cancer in a subject.

In one particular aspect, the cancer treatment is performed in conjunction with determining an expression level of one or a plurality of markers in an exosome sample of the subject, wherein the markers are selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof, and based on the determination made, initiating, continuing, modifying or discontinuing the cancer treatment.

In one specific embodiment, the one or plurality of markers are selected from the group consisting of versican core protein, nidogen-1, pentraxin 3, thrombospondin-1, and any combination thereof. More particularly, the one or plurality of markers suitably comprise versican core protein, nidogen-1 and pentraxin 3 and optionally further include the further biomarker of thrombospondin-1.

In this regard, it would be appreciated that those methods described herein for predicting and/or determining the responsiveness of a cancer to an anti-cancer agent may further include the step of administering to the mammal a therapeutically effective amount of the anti-cancer treatment, such as an anti-cancer agent. In a preferred embodiment, the anti-cancer treatment is administered when the gene and/or protein expression level of the one or plurality of markers described herein indicates or correlates with relatively increased responsiveness of the cancer to the anti-cancer agent.

In other embodiments, the anti-cancer treatment is modified or discontinued when the gene and/or protein expression level of the one or plurality of markers described herein indicates or correlates with the continued presence (e.g., minimal residual disease), progression or recurrence of the cancer or a lack of or reduced responsiveness of the cancer to the anti-cancer treatment.

Suitably, the agent(s) is/are administered to a subject as a pharmaceutical composition comprising a pharmaceutically-acceptable carrier, diluent or excipient. In this regard, any dosage form and route of administration, such as those provided therein, may be employed for providing a subject with the composition of the invention.

Cancer treatments may include drug therapy, such as small organic or inorganic molecules, chemotherapy, antibody, nucleic acid and other biomolecular therapies, radiation therapy, surgery, nutritional therapy, relaxation or meditational therapy and other natural or holistic therapies, although without limitation thereto. Generally, drugs (e.g., small organic or inorganic molecules), biomolecules (e.g antibodies, inhibitory nucleic acids such as siRNA) or chemotherapeutic agents are referred to herein as "anti-cancer therapeutic agents" or "anti-cancer agents".

Methods of treating cancer may be prophylactic, preventative or therapeutic and suitable for treatment of cancer in mammals, particularly humans. As used herein, "treating", "treat" or "treatment" refers to a therapeutic intervention, course of action or protocol that at least ameliorates a symptom of cancer after the cancer and/or its symptoms have at least started to develop. As used herein, "preventing", "prevent" or "prevention" refers to therapeutic intervention, course of action or protocol initiated prior to the onset of cancer and/or a symptom of cancer so as to prevent, inhibit or delay or development or progression of the cancer or the symptom.

The term "therapeutically effective amount" describes a quantity of a specified agent sufficient to achieve a desired effect in a subject being treated with that agent. For example, this can be the amount of a chemotherapeutic agent necessary to reduce, alleviate and/or prevent a cancer or cancer associated disease, disorder or condition. In some embodiments, a "therapeutically effective amount" is sufficient to reduce or eliminate a symptom of a cancer. In other embodiments, a "therapeutically effective amount" is an amount sufficient to achieve a desired biological effect, for example an amount that is effective to decrease or prevent cancer growth and/or metastasis.

Ideally, a therapeutically effective amount of an agent is an amount sufficient to induce the desired result without causing a substantial cytotoxic effect in the subject. The effective amount of an agent useful for reducing, alleviating and/or preventing a cancer will be dependent on the subject being treated, the type and severity of any associated disease, disorder and/or condition (e.g., the number and location of any associated metastases), and the manner of administration of the therapeutic composition.

Suitably, the anti-cancer therapeutic agent is administered to a mammal as a pharmaceutical composition comprising a pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, liposomes and other lipid-based carriers, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991), which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunotherapeutic compositions, proteinaceous vaccines and nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Compositions of the present invention suitable for oral or parenteral administration may be presented as discrete units such as capsules, sachets or tablets each containing a predetermined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgment of the practitioner.

In particular embodiments, the anti-cancer treatment and/or agent may be directed at inhibiting the action of and/or decreasing the expression of the one or plurality of markers.

In other embodiments, the anti-cancer treatment and/or agent may be directed at preventing or inhibiting metastasis of the cancer.

In alternative embodiments, the anti-cancer treatment and/or agent may be directed at genes or gene products other than the one or plurality of markers of the invention. By way of example, the anti-cancer treatment may target genes or gene products that are known to interact, directly or indirectly, with the one or plurality of markers.

In a particular embodiment, the invention provides a "companion diagnostic" with respect to the cancer treatment, whereby the expression level of the one or plurality of markers of the invention provides information to a clinician or the like that is used for the safe and/or effective administration of said cancer treatment.

Suitably, the cancer is of a type hereinbefore described, albeit without limitation thereto.

In particular embodiments, the method further includes the step of comparing the expression level of the one or plurality of markers in the exosome sample to a reference or control exosome expression level of the respective one or plurality of markers, such as hereinbefore described.

Referring to the aforementioned aspects, the method suitably includes the initial step of obtaining the exosome sample from the subject, such as from those biological samples and/or isolation methods hereinbefore described.

In certain embodiments, the method of aforementioned aspects further includes the further step of determining a cancer type in the subject. In this manner, the cancer type may be utilised in determining, for example, cancer aggressiveness, a prognosis, a treatment regime and/or responsiveness to treatment of the cancer in the subject.

In a further aspect, the invention provides a method for identifying or producing an agent for use in the treatment of cancer in a subject including the steps of:

(a) contacting a cell that expresses a marker selected from the group consisting of apolipoprotein E, serine protease 23, versican core protein, hyaluronan and proteoglycan link protein 3, collagen type IV alpha 1 chain, nidogen-1, connective tissue growth factor, collagen type IV alpha 2 chain, carboxypeptidase D, collagen and calcium-binding EGF domain-containing protein 1, pentraxin 3, testican-1, aminoacyl tRNA synthase complex-interacting multifunctional protein 1, thrombospondin-1, biglycan and any combination thereof with a candidate agent; and (b) determining whether the candidate agent modulates the expression and/or an activity of the marker.

In certain embodiments, the candidate agent, at least partly, reduces, eliminates, suppresses or inhibits the expression and/or the activity of the marker.

Suitably, the agent possesses or displays little or no significant off-target and/or nonspecific effects.

Preferably, the agent is an antibody or a small molecule.

Suitably, the marker is selected from the group consisting of versican core protein, nidogen-1, pentraxin 3, thrombospondin-1 and any combination thereof.

In embodiments relating to antibody inhibitors, the antibody may be polyclonal or monoclonal, native or recombinant. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. *Antibodies: A Laboratory Manual*, Cold Spring Harbor, Cold Spring Harbor Laboratory, 1988, which are both herein incorporated by reference.

Generally, antibodies of the invention bind to or conjugate with an isolated protein, fragment, variant, or derivative of the marker. For example, the antibodies may be polyclonal antibodies. Such antibodies may be prepared for example by injecting an isolated protein, fragment, variant or derivative of the marker protein product into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

Monoclonal antibodies may be produced using the standard method as for example, described in an article by Köhler & Milstein, 1975, Nature 256, 495, which is herein incorporated by reference, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the isolated marker protein products and/or fragments, variants and/or derivatives thereof.

Typically, the inhibitory activity of candidate inhibitor antibodies may be assessed by in vitro and/or in vivo assays that detect or measure the expression levels and/or activity of the marker protein in the presence of the antibody.

In some embodiments, modulators such as inhibitors may be rationally designed. These methods may include structural analysis of the marker and the design and/or construction of molecules that bind, interact with or otherwise modulate the activity of the marker. These methods may particularly include computer-aided three-dimensional modeling of the interaction between the candidate modulator and the marker.

In other embodiments, modulators such as small organic molecule inhibitors, this may involve screening of large compound libraries, numbering hundreds of thousands to millions of candidate inhibitors (chemical compounds including synthetic, small organic molecules or natural products, such as inhibitory peptides or proteins) which may be screened or tested for biological activity at any one of hundreds of molecular targets in order to find potential new drugs, or lead compounds. Screening methods may include, but are not limited to, computer-based ("in silico") screening and high throughput screening based on in vitro assays.

Typically, the active compounds, or "hits", from this initial screening process are then tested sequentially through a series of other in vitro and/or in vivo tests to further characterize the active compounds. A progressively smaller number of the "successful" compounds at each stage are selected for subsequent testing, eventually leading to one or more drug candidates being selected to proceed to being tested in human clinical trials.

At the clinical level, screening a candidate agent may include obtaining samples from test subjects before and after the subjects have been exposed to a test compound. The levels in the samples, such as exosome samples, of marker protein may then be measured and analysed to determine whether the levels and/or activity of the marker protein changes after exposure to a candidate agent. By way of example, protein product levels in the samples may be determined by mass spectrometry, western blot, ELISA, electrochemistry and/or by any other appropriate means known to one of skill in the art.

In this regard, candidate agents that are identified of being capable of reducing, eliminating, suppressing or inhibiting the expression level and/or activity of the marker may then be administered to patients who are suffering from cancer. For example, the administration of a candidate agent which inhibits or decreases the activity and/or expression of the marker may treat the cancer and/or decrease the risk of cancer, if the increased activity of the biomarker is responsible, at least in part, for the progression and/or onset of the cancer.

In a final aspect, the invention provides an agent identified or produced by the aforementioned aspect, for use according to the methods described herein.

With respect to the aforementioned aspects, the term "subject" includes but is not limited to mammals inclusive of humans, performance animals (such as horses, camels, greyhounds), livestock (such as cows, sheep, horses) and companion animals (such as cats and dogs). Preferably, the subject is a human.

All computer programs, algorithms, patent and scientific literature referred to herein is incorporated herein by reference.

For the present invention, the database accession number or unique identifier provided herein for a gene or protein, such as those presented herein, as well as the gene and/or protein sequence or sequences associated therewith, are incorporated by reference herein.

So that preferred embodiments of the invention may be fully understood and put into practical effect, reference is made to the following non-limiting examples.

EXAMPLES

Small extracellular vesicles, termed exosomes, have been recently shown to serve as a non-invasive method for potentially identifying cancer. Exosomes are small membrane bound vesicles (30-150 nm in diameter) that are released by all cells, including cancer cells. The protein content of exosomes is dependent on the cell-of-origin and it is now emerging that exosomes represent a viable source of material for diagnostic and prognostic purposes. However, available evidence for specific markers that distinguish between exosomes derived from cancer cells or normal cells is currently lacking. Identifying cancer specific exosome markers could allow the identification of patients with cancer and potentially result in improved survival rates.

Numerous attempts have been made to identify the optimal analysis of human biofluids to identify the presence of cancer including analysis of tumour secreted factors and circulating tumour DNA (ctDNA). Cancer-derived exosomes could serve as superior liquid biomarkers compared to ctDNA due to an increased half-life and the active process of exosome secretion thereby providing a consistent presence of cancer antigens or biomarkers. In the present Example, we describe a comprehensive clinical assay that utilizes cancer-derived exosome proteins for cancer diagnosis. The clinical performance of this assay is highly sensitive and specific and detects cancer at early stage 1, thereby providing opportunities for early-detection and improved survival in numerous patients with cancer.

Cell Culture

Cell line authentication was carried out using short tandem repeat profiling. Isogenic immortalized normal human bronchial epithelial cells (HBEC30KT) transformed with p53 knockdown and Kras v12 overexpression ($30KT^{p53/KRAS}$) were a gift from Dr. Jill Larsen[22,27]. HBECs were cultured in keratinocyte serum free medium (KSFM), supplemented with EGF (5 ng/mL) and bovine pituitary extract (50 mg/L), 37° C. in 5% $CO_2$. All other cell lines were maintained in DMEM or RPMI supplemented with 5% foetal bovine serum, 100 U/mL penicillin and 100 mg/mL streptomycin and incubated at 37° C. in 5%. Cell conditioned media (CCM) was collected from cells cultured in serum-free media. CCM was collected from HBEC cells in KSFM depleted of bovine exosomes through overnight centrifugation at 100,000 $g_{avg}$.

Exosome Isolation and Analysis

Exosomes were isolated and analysed as previously described[8,28]. For exosome for mass spectrometry analysis, CCM was centrifuged at 300 g for 10 minutes at 4° C. and filtered through 0.22 μm filters to remove floating cells and large extracellular vesicles. Clarified CCM was then concentrated to 500 μL and overlaid on a discontinuous iodixanol density gradient and centrifuged for 16 hours at 100,000 $g_{avg}$ at 4° C. Exosome containing fractions were diluted to 20 mL in PBS and centrifuged at 100,000 $g_{avg}$ at 4° C. for 2 hours. The resulting pellet was resuspended in PBS and stored at −80° C. until use. Similarly, all other exosome isolations from in vitro CCM were clarified and concentrated as described above and then purified using size exclusion chromatography. For the isolation of exosomes from human plasma, plasma was thawed at room temperature and prepared by removing remaining platelets and large vesicles by centrifugation at 1,500 g and 10,000 g, for 10 and 20 minutes respectively. Prepared plasma was overlaid on a size exclusion column followed by elution with PBS, concentrated in Amicon® Ultra-4 10 kDa nominal molecular weight centrifugal filter units and stored at −80° C. until use. Exosome isolations from cell culture and human plasma were confirmed with western blot, tunable resistive pulse sensing (TRPS), and transmission electron microscopy as previously described[8].

Antibodies and Reagents

The following antibodies were used for Western blotting: Calnexin (Cell Signaling Technology, 2679S), CD63 (Abcam, ab8219), HSP70 (Transduction Laboratories, 610608). Horseradish peroxidase (HRP)-conjugated secondary antibodies were purchased from Thermo Scientific. THBS 1, NID1, and PTX3 ELISA DuoSets were purchased from R & D Systems, VCAN ELISA kits were purchased from Novus Biologicals. qEV columns were purchased from Izon and stored in PBS (0.1% sodium azide) at 4° C.

Western Blot Analysis

Western blots were performed as previously described[1,2]. Briefly, proteins were resolved by SDS-PAGE, transferred to polyvinylidene fluoride membranes, blocked in 5% non-fat powdered milk in PBS-T (0.5% Tween-20) and probed with antibodies. Protein bands were detected with enhanced chemiluminescence reagent (Amersham ECL Select).

Mass Spectrometry

Exosome preparations were reduced by addition of 10 mM dithiothreitol (4° C. 1-hour, 22° C. 2 hours) in the presence of 2% SDS, protease inhibitors (SigmaAldrich, P8340) and 50 mM Tris.HCl pH 8.8. Samples were then alkylated by the addition of iodoacetamide to 25 mM (22° C. 1-hour) and methanol co-precipitated overnight at −20° C. with trypsin (1:100 enzyme:substrate). Pellets were resuspended in 10% acetonitrile, 40 mM ammonium bicarbonate and digested at 37° C. for 8 hours with further trypsin added after 2 hours (1:100 enzyme:substrate).

LCMS analysis of acidified digests (trifluoroacetic acid) was performed by interfacing a NanoAcquity UPLC (Waters) in front of an Elite Orbitrap ETD mass spectrometer (Thermo Fisher Scientific). Two micro-grams of digest was loaded onto a 20 mm×180 μm Symmetry C18 trap (Waters) and separated over 120 minutes on a 200 mm×75 μm, BEH130 1.7 μm column (Waters) using a series of linear gradients (buffer A: aqueous 0.1% formic acid; buffer B: 0.1% formic acid in acetonitrile) 2% B to 5% B over 5 minutes, 30% B over 75 minutes, 50% B over 10 minutes 95% B over 5 minutes and hold for 6 minutes, re-equilibrate in 2% B. Eluate from the column was introduced into the mass spectrometer through a 10 μm P200P coated silica emitter (New Objective) and Nanospray-Flex source (Proxeon Biosystems A/S). Source voltage 1.8 kV, heated capillary temperature 275° C., using a top 15 method MS acquired in the orbitrap at 120 000 resolution AGC 1E6, MS2 in the ion-trap AGC 1E4, 50 ms maximum injection time. MS1 lock mass of 445.120024 was used.

Protein identification and label-free quantification were performed using MaxQuant (version 1.4.1.2[3]. MaxQuant was used to extract peak lists from the Xcalibur raw files (Thermo Fisher Scientific, Germany) and the embedded database search engine Andromeda[4] was used to assign peptide-to-spectrum matches (PSMs). The database searched consisted of the complete proteome for *Homo sapiens* (88,378 canonical sequences downloaded from www.uniprot.org August 2013). Reversed sequences and the MaxQuant contaminant database were also searched. Label-free quantification was performed, the instrument type was set to Orbitrap, the precursor mass tolerance was set to 20 ppm for the first search, 4.5 ppm for the main search, the fragment ion mass tolerance was set to 0.5 Da, the enzyme specificity was set to trypsin/P, a maximum of two missed cleavages were allowed, carbamidomethyl cysteine was specified as a fixed modification and acetylation of the protein N-terminal, deamidation of asparagine/glutamine and oxidation of methionine were specified as variable modifications. The second peptide search and match between runs were enabled with default settings. For identification, the PSM and protein level FDRs were set to 0.01. Default settings were applied for all other parameters. Protein inference and label-free quantification by spectral counting (including normalisation) were performed as previously described[5].

Patient Cohorts

Retrospective analysis of a patient cohort of patient plasma/serum samples, collected between 2001-2019 was performed.

Statistical Analysis

GraphPad Prism version 6.0, EdgeR version 2.6.10, MedCalc version 16.8.4, and IPA were used for all calculations. Unpaired Student's t-test was used to calculate the difference in expression values of proteins from exosomes in vitro. Subcellular localisation of proteins was generated through IPA (QIAGEN Inc). A negative-binomial exact test was used to assess the mass spectrometry derived spectral counts, where the Benjamini-Hochberg adjustment was applied to control the FDR. Differences with p-values less than 0.05 were considered significant (*p<0.05, p<0.01, *p<0.001), with the exception of a FDR threshold of 0.001.

Results

Generation of an Exosome Protein Signature for Cancer

We postulated that HBECs with an oncogenic mutation would secrete exosomes with a distinct exosome protein profile. We isolated exosomes secreted by normal HBECs and transformed HBECs$^{(p53/KRAS)}$. TEM, nanoparticle tracking and western blotting demonstrated that exosomes displayed typical size distribution and contained canonical exosome markers (FIG. 1A-C). The proteomes of normal and transformed HBECs were then evaluated using mass spectrometry. Label-free quantification by spectral counting identified 15 extracellular proteins that were upregulated in transformed HBECs compared to normal HBECs (FIG. 1D). THBS1, NID1, PTX3, and VCAN were selected for further evaluation and confirmed with ELISA in HBECs (FIG. 1E).

Current clinical management for all solid malignancies is directed by histopathology and/or molecular characteristics of primary tumours. However, expression of biomarkers for classification of tumours can be highly variable, even within an individual tumour. During cancer progression, cancer cells can display a wide array of phenotypes, some of which are caused by epigenetic alterations, oncogenic transformation, or even altered environmental cues. Even within a specified cancer (lung, brain, melanoma), a tumour is a highly heterogeneous disease, reflected by various clinical and molecular classifications. Given this, we evaluated the expression of these 4 proteins in further cancer cell lines to establish if the proteins were universally upregulated in various cancer lines, or specific to particular subsets of cancer cells. To address this, we isolated exosomes from a total of 22 cell lines comprising of; non-small cell lung cancer (NSCLC), glioblastoma (GBM), colorectal (CRC), breast (BCa), prostate (PCa), melanoma (MEL), esophageal (ECa), and ovarian (OVA) cancer. Interestingly, we found that all 4 markers, in particular NID1, were upregulated in cancer cell-derived exosomes compared to normal HBEC exosomes, regardless of cancer-type.

Evaluation of the Exosome Protein Signature in Cancer Patients

We then postulated that oncogenic-induced exosome changes could be utilised as a diagnostic biomarker for disease presence in cancer patients. Exosomes were isolated from the serum/plasma of 250 healthy controls and 497 cancer patients who had been diagnosed with cancers of the lung, brain, colorectum, prostate, melanoma, stomach, and esophagus. The median age of healthy controls and patients at diagnosis was 65.5.

Figure 2:
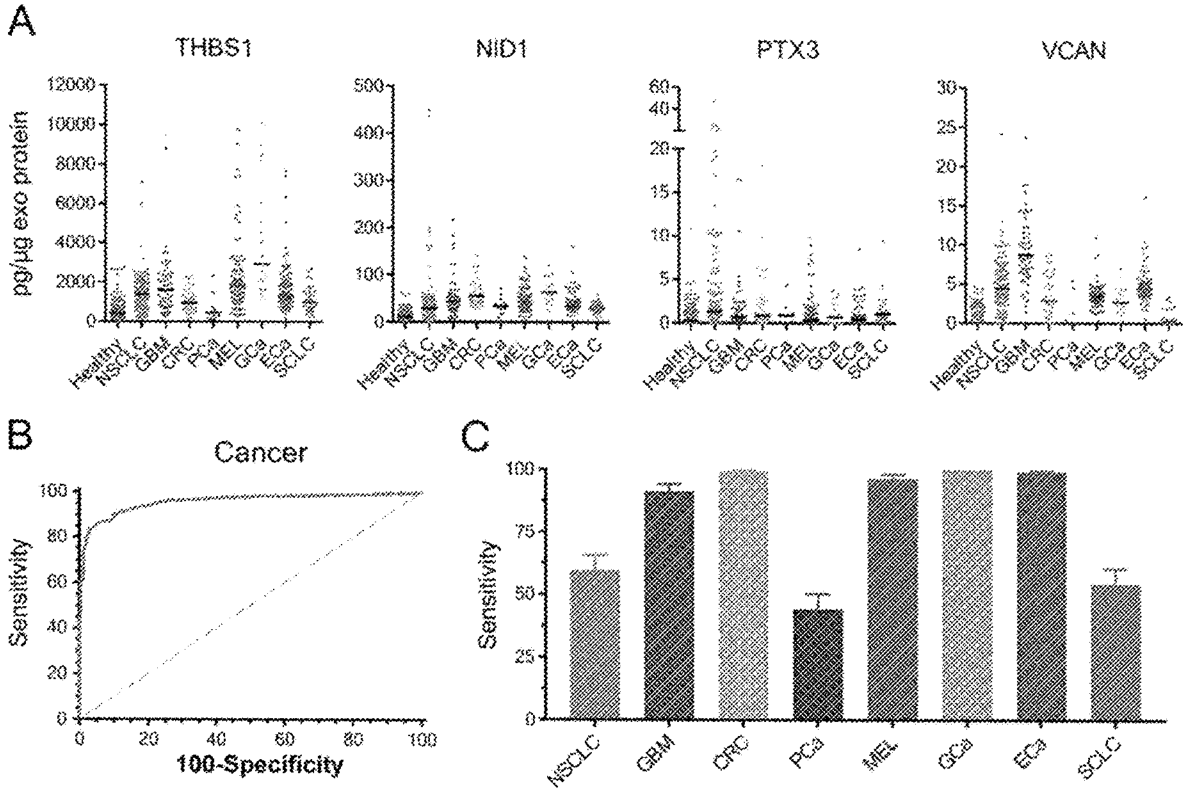
FIG. 2: Oncogenic exosome signature diagnoses cancer in patient plasma. (A) The expression level of THBS1, NID1, PTX3, and VCAN in cancer patients is increased in comparison to healthy controls. (B) Logistic regression demonstrates excellent diagnostic capability of the 4-protein exosomes panel with an AUC of 0.96. (C) The sensitivity of the diagnostic exosomes signature for each cancer was evaluated at a fixed-specificity of 95%. Error bars represent 95% confidence intervals.
Figure 3:
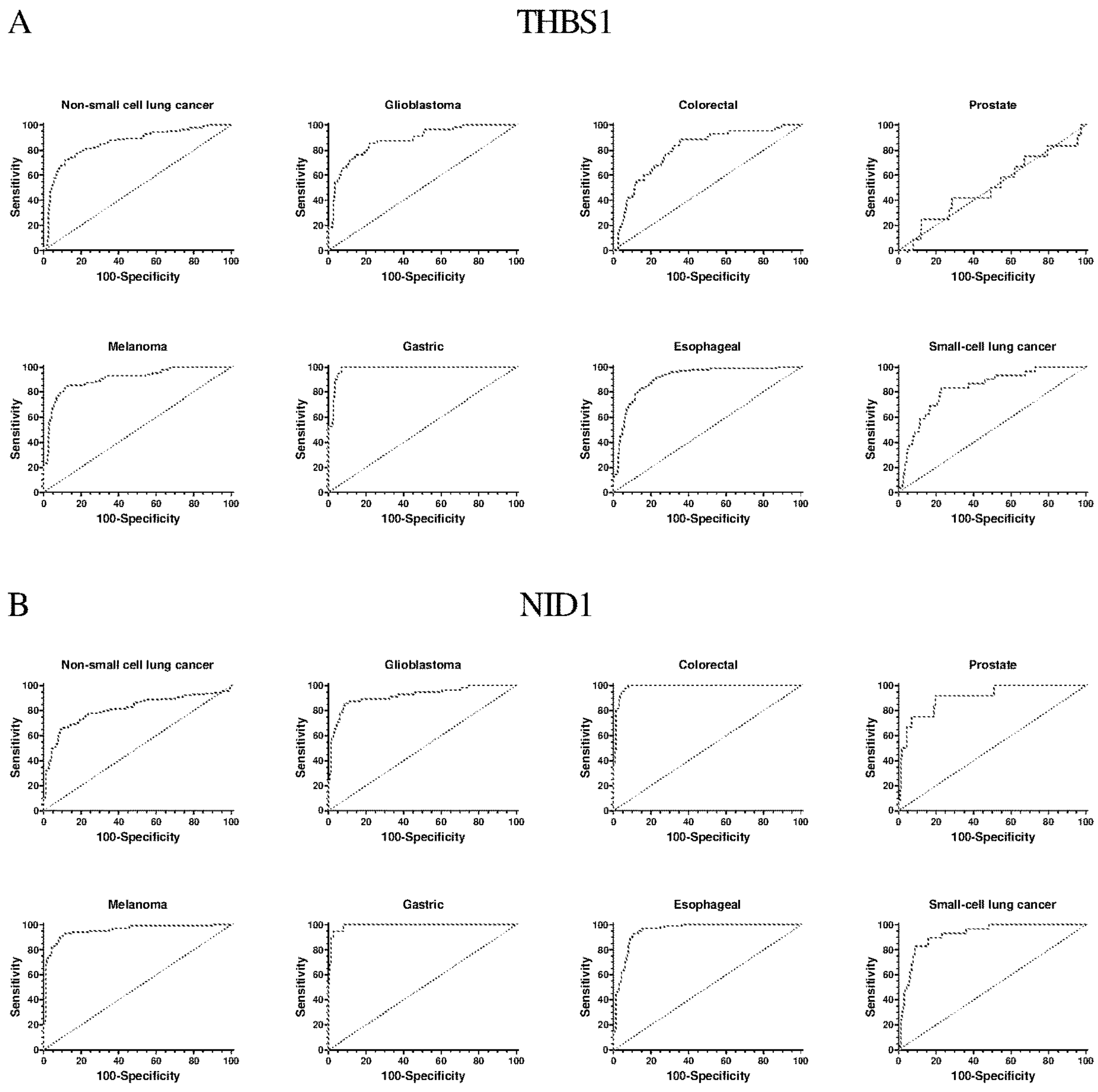
FIG. 3: Evaluating the diagnostic capability of (A)THBS1, (B) NID1, (C) PTX3, and (D) VCAN individually by ELISA shows that each exosomal protein has a range of diagnostic capabilities in Non-Small Cell Lung Cancer, Glioblastoma, Colorectal Cancer, Prostate Cancer, Melanoma, Gastric Cancer, Esophageal Cancer and Small-Cell Lung Cancer, as assessed by receiver operating characteristic (ROC) curves.
Figure 3:
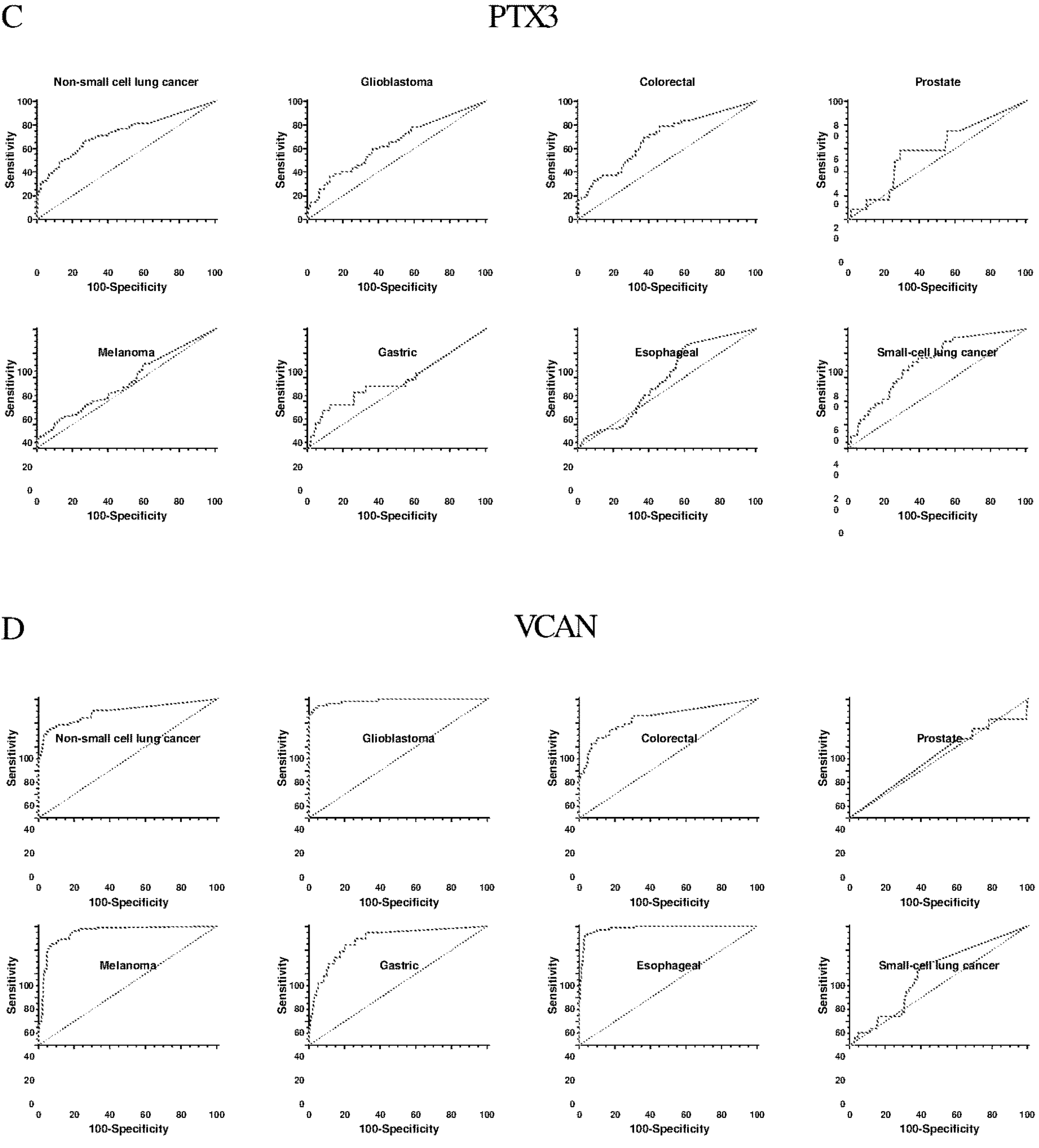

Interestingly, the combined 4 protein exosome signature (THBS1, NID1, PTX3, and VCAN) was increased in exosomes derived from cancer subjects who compared to healthy controls (FIG. 2A). Each protein from the exosome signature had a range of diagnostic capabilities in the different cancer cohorts as assessed by receiver operating characteristic (ROC) curves (FIG. 3). Interestingly, using a combination of the signature proteins using logistic regression we were able to generate an excellent separation of healthy individuals and cancer patients with an area under the curve (AUC) of 0.96 (FIG. 2B). Importantly, at a fixed specificity of 95%, the median sensitivity of the diagnostic exosome signature in the 8 cancer types was 77.6% (95% CI: 72.0%, 82.3%). This ranged from 44% in prostate cancer to 100% in gastric cancer (FIG. 2C).

Figure 4:
FIG. 4: Sensitivity of the diagnostic exosome signature by tumour stage. A, The diagnostic exosome signature is capable of detecting early stage I patients as well as later stage II-IV patients in NSCLC, esophageal and gastric cancer at 95% specificity. Error bars represent 95% confidence intervals.
Figure 4:
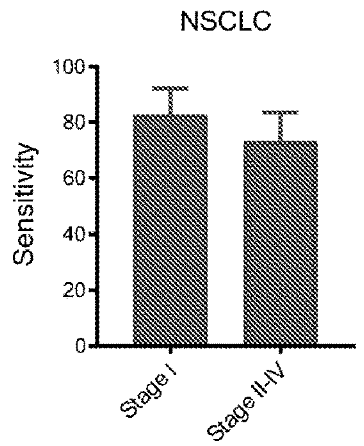
Figure 4:
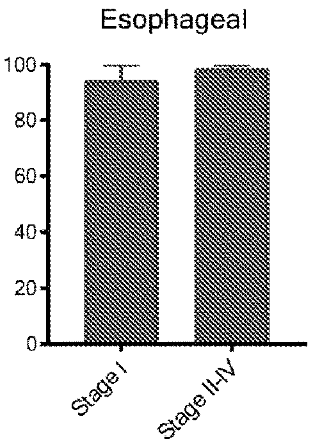
Figure 4:
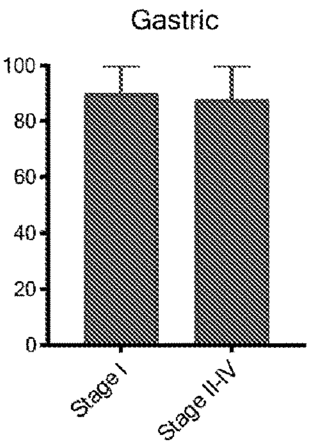

We next wanted to assess the capabilities of the diagnostic exosomes signature in identifying early-stage cancer patients. For a liquid biopsy to be of the most benefit it needs to identify patients at the earliest possible stage to provide a large improvement in overall cancer survival. We were able to evaluate the sensitivity of the exosome biomarker in stage I compared to stage II-IV in NSCLC, oesophageal, and gastric cancer. Importantly, the sensitivity at 95% specificity was comparable to later stages in all 3 cancers (FIG. 4), demonstrating that the diagnostic exosome signature is capable of identifying early-stage cancer patients.

Figure 5:
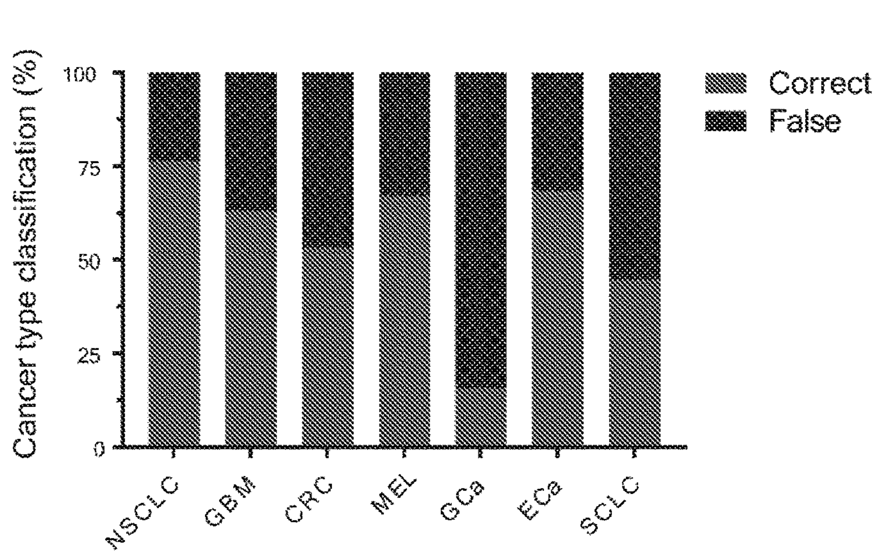
FIG. 5: Machine learning can help identify cancer-type. Percentage of patients identified correctly or incorrectly for cancer-type demonstrates that the exosome signature can help identify the type of cancer present.

Recently, CancerSEEK (REF) demonstrated that liquid biopsies can be used to identify not only the presence on cancer, but also the tumour-type for clinical follow-up using machine learning. We therefore investigated whether our exosomes signature was also capable of correctly identifying the type of cancer that a patient had. The accuracy of the test varied widely with NSCLC being the most accurate prediction and gastric cancer being the lowest (FIG. 5).

REFERENCES

1. Lobb, R. J., et al. Optimized exosome isolation protocol for cell culture supernatant and human plasma. *J Extracell Vesicles* 4, 27031 (2015).
2. Lobb, R. J., et al. Exosomes derived from mesenchymal non-small cell lung cancer cells promote chemoresistance. *International journal of cancer* 141, 614-620 (2017).
3. Cox, J. & Mann, M. MaxQuant enables high peptide identification rates, individualized p.p.b.-range mass accuracies and proteome-wide protein quantification. *Nature biotechnology* 26, 1367-1372 (2008).
4. Cox, J., et al. Andromeda: a peptide search engine integrated into the MaxQuant environment. *Journal of proteome research* 10, 1794-1805 (2011).
5. Dave, K. A., et al. A comprehensive proteomic view of responses of A549 type II alveolar epithelial cells to human respiratory syncytial virus infection. *Molecular & cellular proteomics*: MCP 13, 3250-3269 (2014).

The invention claimed is:

1. A method of diagnosing a cancer or recurrence of a cancer in a subject, said method including the step of determining an expression level of a plurality of markers in an exosome sample of the subject, wherein the markers are selected from the group consisting of VCAN, NID1, PTX3, and THBS1, and wherein the expression level of the plurality of markers indicates or correlates with a diagnosis or recurrence of the cancer.

2. The method of claim 1, including the further step of determining a cancer type in the subject diagnosed with the cancer, wherein the expression level of the plurality of markers indicates or correlates with the cancer type.

3. The method of claim 1, including the further step of determining the aggressiveness of a cancer in the subject, wherein the expression level of the plurality of markers indicates or correlates with a level of aggressiveness of the cancer.

4. The method of claim 1, including the further step of determining a prognosis for a cancer in the subject, wherein the expression level of the plurality of markers indicates or correlates with a less or more favourable prognosis for said cancer.

5. The method of claim 1, wherein a relatively decreased or unchanged expression level of the one or plurality of markers indicates or correlates with a more favourable prognosis and/or a less aggressive cancer; and/or a relatively increased expression level of the plurality of markers indicates or correlates with a less favourable prognosis and/or a highly aggressive cancer.

6. The method of claim 1, which includes the further step of diagnosing said subject as having: (i) a highly aggressive cancer or a less aggressive cancer; and/or (ii) a less favourable prognosis or a more favourable prognosis.

7. A method of predicting and/or determining the responsiveness of a cancer to an anti-cancer treatment in a subject, said method including the step of determining an expression level of a plurality of markers in an exosome sample of the subject, wherein the markers are selected from the group consisting of VCAN, NID1, PTX3, and THBS1 and an altered or modulated expression level of the plurality of markers indicates or correlates with relatively increased or decreased responsiveness of the cancer to the anti-cancer treatment.

8. The method of claim 1, which includes the further step of treating the cancer in the subject based on the determination made, wherein the treatment includes initiating, continuing, modifying, or discontinuing an anti-cancer treatment.

9. The method of claim 8, wherein the anti-cancer treatment comprises administration to the subject of a therapeutically effective amount of an anti-cancer agent that decreases the expression and/or an activity of the plurality of markers.

10. The method of claim 1, further including the step of obtaining the exosomal sample from the subject.

11. The method of claim 1, further including the step of comparing the expression level of the plurality of markers in the exosome sample to a reference exosome expression level of the respective plurality of markers.

12. The method of claim 1, wherein the cancer and/or cancer type is selected from the group consisting of lung cancer (e.g., small-cell lung cancer), such as NSCLC and SCLC, breast cancer, colorectal cancer, prostate cancer, gastric cancer, skin cancer, such as melanoma, brain cancer, such as glioblastoma multiforme (GBM), ovarian cancer, esophageal cancer and any combination thereof.

13. A composition comprising an exosomal sample from claim 10, and a reagent for determining the expression level of a plurality of VCAN, NID1, PTX3, and THBS1.

14. The composition of claim 13, wherein the exosomal sample comprises reagents for determining the level of each of VCAN, NID1, PTX3, and THBS1, in a single composition.

15. The composition of claim 13, wherein the exosomal sample comprises reagents for determining the level of each of VCAN, NID1, PTX3, and THBS1, in separate compositions.

16. A diagnostic kit or test device for use in a method of diagnosing a cancer or recurrence of a cancer in a subject, said method including the step of determining an expressing level of a plurality of markers in an exosome sample of the subject, wherein the markers are selected from the group consisting of VCAN, NID1, PTX3, and THBS1 and wherein the expression level of the plurality of markers indicates or correlates with a diagnosis or recurrence of the cancer, the diagnostic kit or test device comprising a plurality of specific binding members, each of which selectively binds to a marker selected from the group consisting of VCAN, NID1, PTX3, and THBS1 and one or more reagents for detecting said specific binding members or one or more reagents for detecting and/or quantifying formation of a complex formed by said specific binding member and said marker.

17. The diagnostic kit or test device according to claim 16, wherein the markers include each of VCAN, NID1, PXT3, and THBS1.

18. The diagnostic kit or test device according to claim 16, wherein the markers include each of VCAN, NID1, and PXT3.

19. The diagnostic kit or test device according to claim 16, wherein the markers include each of VCAN, NID1, and THBS1.

20. The diagnostic kit or test device according to claim 16, wherein the markers include each of NID1, PXT3, and THBS1.

21. The diagnostic kit or test device according to claim 16, wherein the markers further comprise one or more of APOE, PRZSS23, HAPLN3, COL4A1, CTGF, COL4A2, CPD, CCBE1, SPOCK1, AIMP1, and BGN.

22. The diagnostic kit or test device according to claim 16, wherein the cancer is selected from the group consisting of lung cancer, breast cancer, colorectal cancer, prostate cancer, gastric cancer, skin cancer, brain cancer, ovarian cancer, esophageal cancer, and any combination thereof.

* * * * *